US00PP22654P2

(12) United States Plant Patent
Korlipara

(10) Patent No.: US PP22,654 P2
(45) Date of Patent: Apr. 17, 2012

(54) ***LEUCANTHEMUM* PLANT NAMED 'VICTORIAN SECRET'**

(50) Latin Name: *Leucanthemum×superbum*
Varietal Denomination: Victorian Secret

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,585

(22) Filed: Nov. 17, 2010

(51) Int. Cl.
*A01H 5/00* (2006.01)

(52) U.S. Cl. ..... Plt./285

(58) Field of Classification Search ..... Plt./285
See application file for complete search history.

*Primary Examiner* — Kent L Bell
(74) *Attorney, Agent, or Firm* — Jondle & Associates, P.C.

(57) ABSTRACT

A new and distinct *Leucanthemum* plant named 'Victorian Secret' characterized by daisy type inflorescences with multiple layers of white ray florets and yellow orange disc florets, excellent bloom size, a medium, compact habit, well-branched flower stalks giving repeat bloom all summer, and excellent vigor.

1 Drawing Sheet

Botanical denomination: *Leucanthemum×superbum.*
Variety designation: 'Victorian Secret'.

The present invention relates to a new and distinct cultivar of *Leucanthemum* and given the cultivar name 'Victorian Secret'. *Leucanthemum* is in the family Asteraceae. This new cultivar originated from a controlled cross between unnamed, proprietary *Leucanthemum×superbum* seedlings. The breeding plan was to make good double inflorescences and compact habits. The new cultivar was selected from many seedlings and clearly "stood out" for these characteristics.

Compared to *Leucanthemum* 'Paladin' (U.S. Plant Pat. No. 21,844), the new cultivar has a lower more compact habit and inflorescences that have more ray florets making the layers look thicker like an Edwardian collar.

This new *Leucanthemum* cultivar is distinguished by:

1. daisy type inflorescences with multiple layers of white ray florets and yellow orange disc florets,
2. excellent bloom size,
3. a medium, compact habit,
4. well-branched flower stalks giving repeat bloom all summer,
5. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a 2 year old plant growing in the ground in full sun in the trial field in mid July in Canby, Oreg.

DETAILED PLANT DESCRIPTION

The following is a detailed description of the new *Leucanthemum* cultivar based on observations of 18-month-old specimens growing in two gallon containers in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:
- *Type.*—Herbaceous perennial.
- *Hardiness.*—USDA Zones 4 to 9.
- *Size.*—45 cm wide and 51 cm tall to top of inflorescences.
- *Form.*—Basal clump.
- *Vigor.*—Excellent.

Stem (flowering):
- *Type.*—Ascending.
- *Size.*—Grows to 50 cm tall to a terminal inflorescence and 9 mm wide at base.
- *Internode length.*—2 to 3 cm.
- *Surface texture.*—Pubescent.
- *Color.*—Yellow Green 146B except on older stems at the base where Greyed Purple 187B.

Leaf (basal):
- *Type.*—Simple.
- *Shape.*—Oblanceolate.
- *Arrangement.*—Basal.
- *Blade size.*—Grows to 12 cm long and 2.2 cm wide.
- *Margins.*—Coarsely serrate.
- *Apex.*—Acute.
- *Base.*—Attenuate, continuing down petiole.
- *Petiole.*—Grows to 6 cm long and 4 mm wide, pubescent, color closest to Yellow Green 146D.
- *Surface texture.*—Pubescent on both sides.
- *Venation.*—Pinnate.
- *Color.*—Top and bottom side, Green 137B.

Leaf (stem):
- *Type.*—Simple, no petiole.
- *Shape.*—Lanceolate.
- *Arrangement.*—Alternate.
- *Blade size.*—Grows to 9 cm long and 17 mm wide.
- *Margins.*—Coarsely serrate on top ⅔, entire on bottom ⅓.

*Apex.*—Acute.

*Base.*—Clasping.

*Surface texture.*—Pubescent on both sides.

*Venation.*—Pinnate.

*Color.*—Topside, Green N137A, bottom side Green 147B.

Inflorescence:

*Type.*—Composite on terminal stalked heads.

*Number of flowering stems per plant in summer.*—About 30.

*Flowering stem.*—Grows to 50 cm tall from the base of the plant to the terminal inflorescence to the base of an inflorescence; branched, from 1 to 5 inflorescences per stem; leafy all the way up the stem; diameter growing to 7 mm wide near the inflorescence head; pubescent; Yellow Green 146B except on older stems at the base were Greyed Purple 187B.

*Size.*—Grows to 8.5 cm wide and 4 cm deep.

*Form.*—Ray florets emerge outward from various angles giving the layers a thicker look, mature disc is slightly rounded.

*Immature inflorescence.*—1.7 cm wide and 2 cm deep, outer ray florets held vertically and inner ray florets tilted inward and rolled up so only the back color shows, Yellow 4D.

*Ray florets.*—With 1 pistil and no stamen, about 150 normal size in number (and 6 to 15 smaller size near the disc florets), oblanceolate, obtuse, entire, attenuate, grows to 3 cm long and 9 mm wide, glabrous on both sides; top and bottom side of inner and outer ray florets White NN155B with base Yellow Green 144B; pistil 6.5 mm long, ovary 1.5 mm long, Yellow Green 145D, style 4.5 mm long, Grayed Yellow 160C, 2 branched stigma 0.5 mm long, Brown 200D.

*Disc.*—Slightly concave becoming convex, becoming 8 mm deep and 32 mm wide with maturity, Yellow Orange 15B.

*Disc florets.*—About 360 in number, each 7 mm long and 1.5 mm wide, corolla tubular campanulate, 4.5 mm long and 1.5 mm wide, 5 lobed, glabrous, Yellow Orange 15B; pistil 1, 7 mm long, ovary 2 mm long and Yellow Green 145A, style 3 mm long and Yellow Green 145A, 2 branched stigma 1 mm long and Yellow Orange 16B; stamen 5 in number, 3 mm long and Yellow Orange 14B, pollen Yellow Orange 14B.

*Phyllaries.*—In 3 imbricate whorls, area 3.9 cm wide and 7 mm deep, lobes lanceolate in shape, grow to 7 mm long and 3 mm wide, Yellow Green 147B, margin membranous and Greyed Purple 187A, tip obtuse, glabrous.

*Receptacle.*—Grows to 12 mm wide and 4 mm deep, Yellow Green 145C.

*Bloom period.*—June through October in Canby, Oreg.

*Fragrance.*—None.

*Lastingness.*—Each inflorescence lasts about two weeks in Canby, Oreg.

Seeds: None seen

*Fertility.*—Poor.

Disease and pests: *Leucanthemum* are susceptible to aphids and leaf spots. These have not been observed on plants grown under commercial conditions in Canby, Oreg. No resistances are known.

I claim:

1. A new and distinct *Leucanthemum* plant as herein illustrated and described.

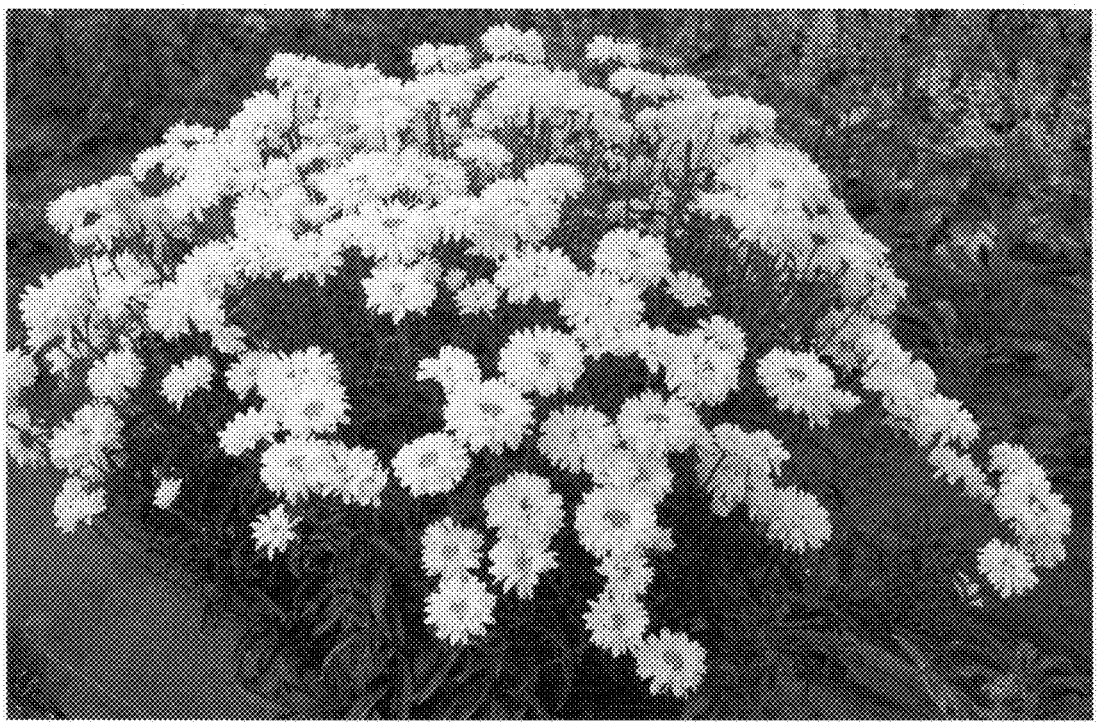

* * * * *